(12) United States Patent
Cavazos Sepulveda et al.

(10) Patent No.: US 12,253,459 B2
(45) Date of Patent: Mar. 18, 2025

(54) IN-SITU MONITORING OF CHEMICAL FINGERPRINTS IN OILFIELD APPLICATIONS

(71) Applicant: SAUDI ARABIAN OIL COMPANY, Dhahran (SA)

(72) Inventors: Adrian Cesar Cavazos Sepulveda, San Pedro Garza Garcia (MX); Damian Pablo San Roman Alerigi, Dhahran (SA); Jose Oliverio Alvarez, Houston, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 665 days.

(21) Appl. No.: 17/490,348

(22) Filed: Sep. 30, 2021

(65) Prior Publication Data
US 2023/0100258 A1 Mar. 30, 2023

(51) Int. Cl.
*G01N 21/27* (2006.01)
*E21B 49/08* (2006.01)
(Continued)

(52) U.S. Cl.
CPC ......... *G01N 21/27* (2013.01); *E21B 49/0875* (2020.05); *G01N 21/35* (2013.01);
(Continued)

(58) Field of Classification Search
CPC ............... G01N 21/27; G01N 33/2823; G01N 2201/129; E21B 49/0875; G01V 8/02
(Continued)

(56) References Cited

U.S. PATENT DOCUMENTS 10,094,214 B2 * 10/2018 Tackmann ........... G01N 21/552
11,840,923 B2 * 12/2023 Jones ................ C23C 16/45536
(Continued)

FOREIGN PATENT DOCUMENTS

| WO | 2016145127 A1 | 9/2016 |
| WO | 2018005465 A1 | 1/2018 |
| WO | 2020231932 A1 | 11/2020 |

OTHER PUBLICATIONS

Schädle, Thomas, et al., "Monitoring dissolved carbon dioxide and methane in brine environments at high pressure using IR-ATR spectroscopy", Analytical Methods, Royal Society of Chemistry, 2016 (7 pages).
(Continued)

*Primary Examiner* — Jonathan M Hansen
*Assistant Examiner* — Noah J. Haney
(74) *Attorney, Agent, or Firm* — Osha Bergman Watanabe & Burton LLP

(57) ABSTRACT

A system for monitoring a composition includes: an electromagnetic source that emits a beam; one or more evanescent field sensing element inside a tubular structure, arranged in series along a flow direction of the composition, and configured to be in direct contact with the composition; a waveguide that directs at least a portion of the beam to the evanescent field sensing element as an incident beam; and a detector configured to obtain a spectral distribution of the fingerprint beam. The evanescent field sensing element provides partial or total internal reflection of the incident beam at an interface between the evanescent field sensing element and the composition, and the incident beam interacts with the composition to form a fingerprint beam.

12 Claims, 12 Drawing Sheets

(51) Int. Cl.
*G01N 21/35* (2014.01)
*G01N 21/552* (2014.01)
*G01N 21/85* (2006.01)
*G01N 33/28* (2006.01)
*G01V 8/02* (2006.01)

(52) U.S. Cl.
CPC ....... *G01N 21/552* (2013.01); *G01N 21/8507* (2013.01); *G01N 33/2823* (2013.01); *G01V 8/02* (2013.01); *G01N 2021/3595* (2013.01); *G01N 2021/8528* (2013.01); *G01N 2201/129* (2013.01)

(58) Field of Classification Search
USPC .......................................................... 356/70
See application file for complete search history.

(56) References Cited

U.S. PATENT DOCUMENTS

| 2008/0314138 | A1 | 12/2008 | Brady |
| 2010/0177310 | A1 | 7/2010 | Difoggio |
| 2011/0261363 | A1* | 10/2011 | Picque .................... G01J 3/453 356/451 |
| 2012/0170023 | A1* | 7/2012 | Szobota ............... G01N 21/552 356/51 |
| 2015/0346087 | A1* | 12/2015 | Skinner ................ G01N 21/255 250/206 |
| 2017/0176324 | A1* | 6/2017 | Perkins .................. G01N 21/25 |
| 2018/0073355 | A1* | 3/2018 | Bhongale .............. G01J 3/0218 |
| 2020/0096429 | A1* | 3/2020 | Andersen ............... G01N 13/02 |
| 2020/0363320 | A1* | 11/2020 | Bhongale .............. E21B 47/135 |

OTHER PUBLICATIONS

Tittel, F. K., et al., "Recent advances of mid-infrared compact, field deployable sensors and their real world applications in the petrochemical industry, atmospheric chemistry and security", ResearchGate, Conference Paper, Jan. 2016 (3 pages).

Villares, Gustavo, et al., "Dual-comb spectroscopy based on quantum-cascade-laser frequency combs", nature communications, 2014 (9 pages).

* cited by examiner

IN-SITU MONITORING OF CHEMICAL FINGERPRINTS IN OILFIELD APPLICATIONS

BACKGROUND

Absorption, transmittance, and reflection of electromagnetic radiation may be utilized in characterization of chemical fingerprints for gases, liquids, and solids. The electromagnetic radiation, having a frequency ranging from gamma and X-rays to micro- and radio waves, may be incorporated into photonic sensors for oil and gas applications. Real-time in-depth monitoring of the downhole composition, including the oil being produced, the water cut, the surrounding environment, and the presence of compounds that impact corrosion (e.g., $H_2S$ and $CO_2$), allows optimization of drilling parameters for maximum production and minimum maintenance.

When a beam of electromagnetic radiation travels from a medium of high refractive index (i.e., evanescent field sensing element) to a medium of low refractive index (e.g., target) at an angle of incidence, an evanescent wave is formed at the interface. At least a portion of the beam is reflected back into the low refractive index medium, which is known as partial internal reflection. When an angle of incidence is greater than a critical angle, the partial internal reflection becomes total internal reflection. At positions where internal reflection occurs, the evanescent wave penetrates with an exponentially decaying amplitude into the adjacent environment. As a result, the evanescent wave directly interacts with the target at the interface, causes changes in the energy distribution (i.e., intensity) of the beam, and generates an absorption spectrum reflecting the chemical fingerprints.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a system for monitoring a composition. The system comprises: an electromagnetic source that emits a beam; one or more evanescent field sensing element inside a tubular structure, arranged in series along a flow direction of the composition, and configured to be in direct contact with the composition; a waveguide that directs at least a portion of the beam to the evanescent field sensing element as an incident beam; and a detector configured to obtain a spectral distribution of the fingerprint beam. The evanescent field sensing element provides partial or total internal reflection of the incident beam at an interface between the evanescent field sensing element and the composition, and the incident beam interacts with the composition to form a fingerprint beam.

In one aspect, embodiments disclosed herein relate to a method of monitoring a composition. The method comprises: placing one or more evanescent field sensing element in series along a flow direction of the composition; contacting the evanescent field sensing element with the composition such that, due to the arrangement of the evanescent field sensing element in series along the flow direction, turbulence in the wellbore composition is generated; directing an incident beam to the evanescent field sensing element; generating an evanescent field at an interface between the evanescent field sensing element and the composition, where the incident beam interacts with the composition to form a fingerprint beam; detecting spectral distribution of the fingerprint beam to monitor the composition in real-time; and transmitting the spectral distribution to a control unit.

In one or more embodiments, the evanescent field sensing element is modified with meta-materials or meta-surfaces in forms of a 1-dimensional or 2-dimensional array of microstructures of particular shape.

Other aspects and advantages of the claimed subject matter will be apparent from the following description and the appended claims.

DETAILED DESCRIPTION

Figure 1:
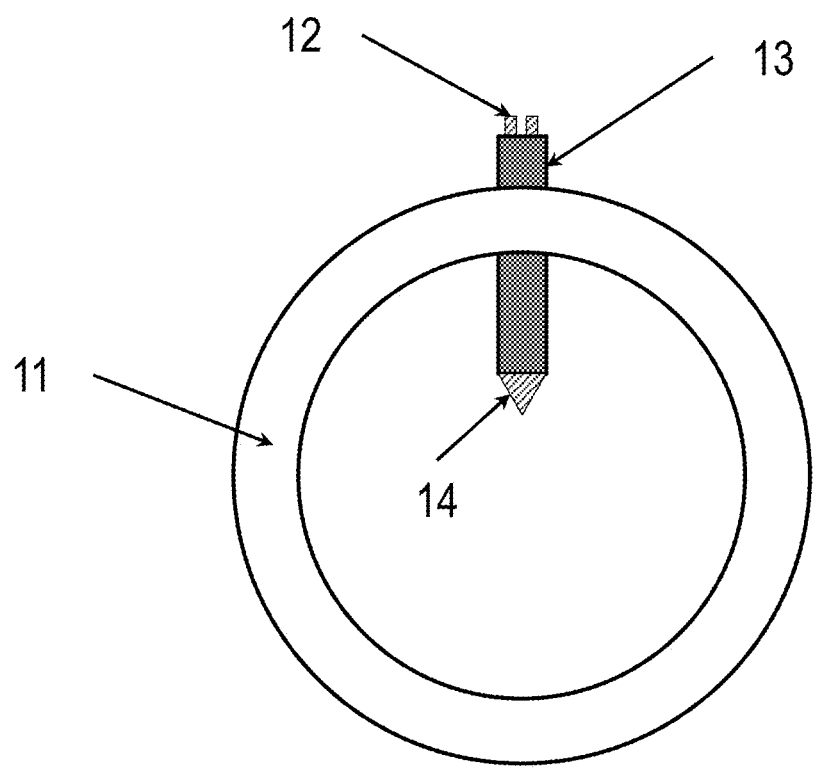
FIG. 1 shows an evanescent field sensing element according to one or more embodiments.

Specific embodiments of the disclosure will now be described in detail with reference to the accompanying figures. Like elements in the various figures are denoted by like reference numerals for consistency.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Embodiments disclosed herein relate generally to systems and methods based on downhole deployment of evanescent field sensing elements to analyze the chemical fingerprints of downhole compositions in real-time and in-situ. The systems and methods utilize one or more of evanescent field sensing elements, frequency combs, and Fourier transform techniques. For example, the system may utilize dual-comb spectroscopy (DCS), Fourier transform infrared spectroscopy (FTIR), attenuated total reflectance (ATR), or any combination thereof for real-time in-situ monitoring of downhole compositions.

The system according to one or more embodiments of the present disclosure integrates the evanescent field sensing elements into downhole structures, providing a monitoring solution with ensured thermal and mechanical stability. By incorporating frequency comb and Fourier transform technologies, the system may advantageously provide higher selectivity and sensitivity. An arrangement of evanescent field sensing elements in series effectively enhances fluid mixing by increasing turbulence thereby reducing the influence of the boundary layer on the sensing.

According to one or more embodiments, the system for monitoring a downhole composition may include an evanescent field sensing element. The evanescent field sensing element is a medium having a higher refractive index than the surrounding environment, providing internal reflection within the media and forming an evanescent field at the interface of the evanescent field sensing element and chemicals in the surrounding environment (downhole compositions).

According to one or more embodiments, one or more evanescent field sensing elements may be disposed inside, on, as a portion of, or outside a downhole or surface structure. As referred to herein, a downhole structure is generally a tubular structure that carries downhole fluid, such as oil, gas, condensate, and water. The downhole structure may be a piping, a tubing, a liner, or a casing. The evanescent field sensing element may be attached to the wall of the downhole structure or disposed inside the downhole structure at different depth. The evanescent field sensing element is in directly contact with downhole compositions for continuous monitoring. The downhole compositions may be gases or liquids. In one or more embodiments, the evanescent field sensing element may be embedded in a cladding. At least a part of the evanescent field sensing element is exposed to the downhole environment. The evanescent field sensing element may have a configuration of any shape or arrangement, from 0 dimensional to 3 dimensional. The evanescent field sensing element may have various configurations including points, tips, prisms, lines, rods, thin films, rings, half-spheres, spheres, rectangles, helices, polyhedrons, etc.

In one or more embodiments, the evanescent field sensing element may have a point configuration inserted into a downhole structure. FIG. 1 shows a configuration of evanescent field sensing element according to one or more embodiments. An evanescent field sensing element 14, having a point configuration, is inserted into a downhole structure 11. One or more waveguides 12 may be used to guide an incident beam from an electromagnetic source to the evanescent field sensing element 14 and guide a fingerprint beam from the evanescent field sensing element 14 to a detector. The evanescent field sensing element 14 is arranged at an end of the waveguide and exposed to downhole environment. Optionally, the waveguide and/or the evanescent field sensing element may be partially embedded in a cladding 13. In one or more embodiments, a plurality of evanescent field sensing elements may be inserted into the downhole structure at different positions, for example, in series along a flow direction of downhole fluids or at different depths. The waveguide 12 and the evanescent field sensing element 14 may be made of a same material or different materials.

Figure 2:
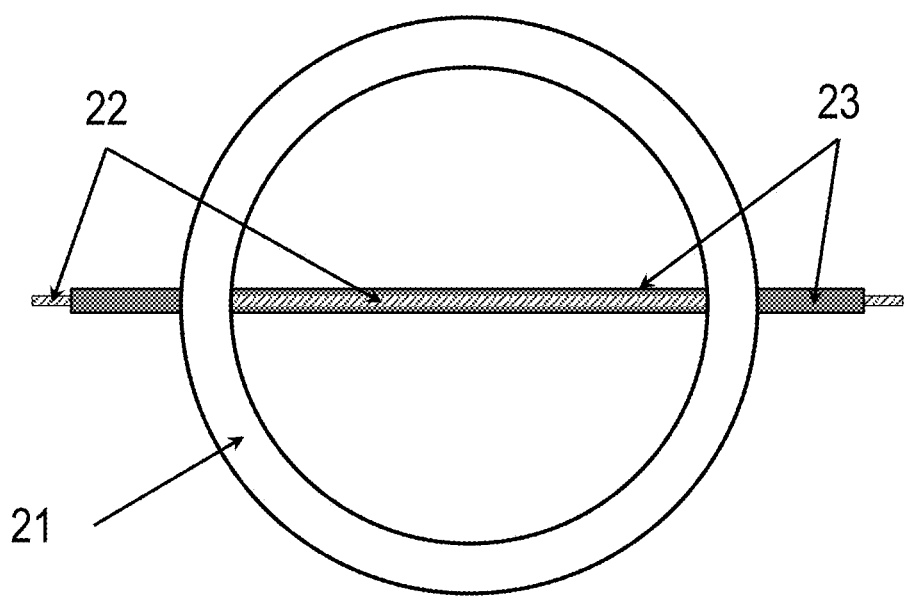
FIG. 2 shows an evanescent field sensing element according to one or more embodiments.

The evanescent field sensing element of the present disclosure may have a line configuration. FIG. 2 shows an arrangement of an evanescent field sensing element according to one or more embodiments. The evanescent field sensing element 22 having a line (or cylinder) shape is arranged inside a downhole structure 21 in a direction along or perpendicular to a flow direction of downhole fluids. In one or more embodiments, the evanescent field sensing element is embedded in a cladding 23, with at least a part of the evanescent field sensing element exposed to downhole environment, enabling interaction with a target at the interface. Alternatively, the evanescent field sensing element may be arranged in the downhole structure without cladding. An incident beam may be directed from an electromagnetic source to one end of the evanescent field sensing element and a fingerprint beam may be directed from the other end of the evanescent field sensing element to a detector.

Figure 3:
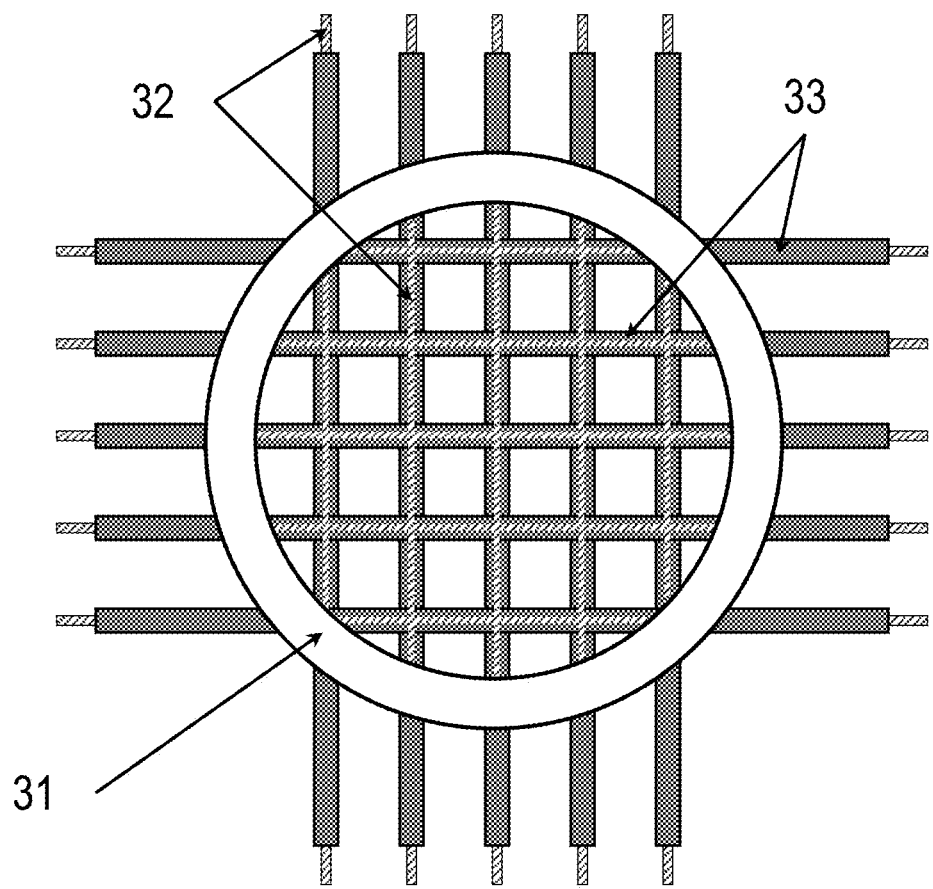
FIG. 3 shows an evanescent field sensing element according to one or more embodiments.

In one or more embodiments, the evanescent field sensing element may have a configuration comprising a plurality of lines arranged in a particular pattern. For example, FIG. 3 shows an arrangement of evanescent field sensing elements according to one or more embodiments. A plurality of evanescent field sensing elements 32 each having a line (or cylinder) shape may form a grid in a downhole structure 31. At least part of each line shape element is exposed to downhole environment for monitoring downhole compositions. In one or more embodiments, the evanescent field sensing elements 32 may be embedded in claddings 33, with at least a part of each evanescent field sensing element exposed to downhole environment, enabling interaction with a target at the interface. In one or more embodiments, a plane formed by the grid of evanescent field sensing elements is perpendicular to a flow direction of downhole fluids.

Figure 4:
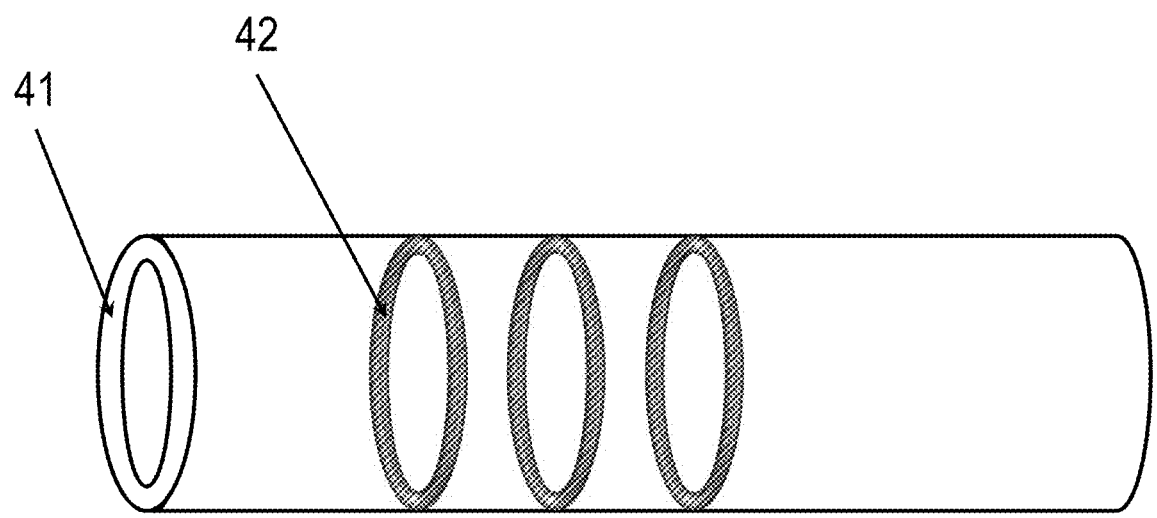
FIG. 4 shows an evanescent field sensing element according to one or more embodiments.
Figure 5:
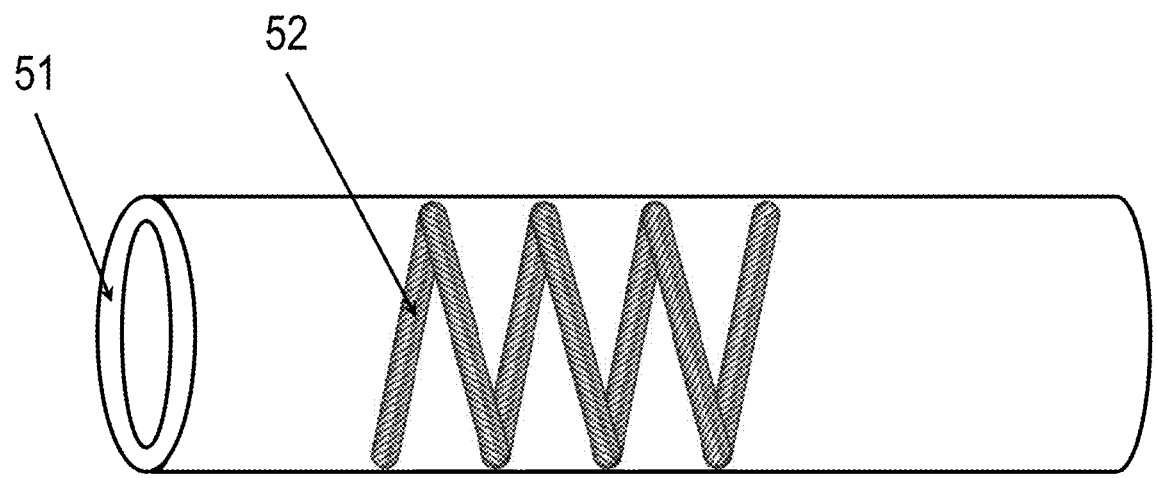
FIG. 5 shows an evanescent field sensing element according to one or more embodiments.

In one or more embodiments, the evanescent field sensing element may have a curved line shape, for example, ring or helix. FIG. 4 shows an arrangement of evanescent field sensing elements according to one or more embodiments. An evanescent field sensing element 42 having a ring shape may be arranged inside a downhole structure 41. The evanescent field sensing element may be attached to an inner wall of the downhole structure. In one or more embodiments, a plurality of evanescent field sensing elements 42 each having a ring shape may be arranged in the downhole structure 41 in series along a flow direction of downhole fluids. FIG. 5 shows an arrangement of an evanescent field sensing according to one or more embodiments. An evanescent field sensing element 52 having a helix shape may be arranged inside a downhole structure 51. The evanescent field sensing element may be attached to an inner wall of the downhole structure. The evanescent field sensing element forms a plurality of curves arranged in series along a flow direction of downhole fluids.

Figure 6:
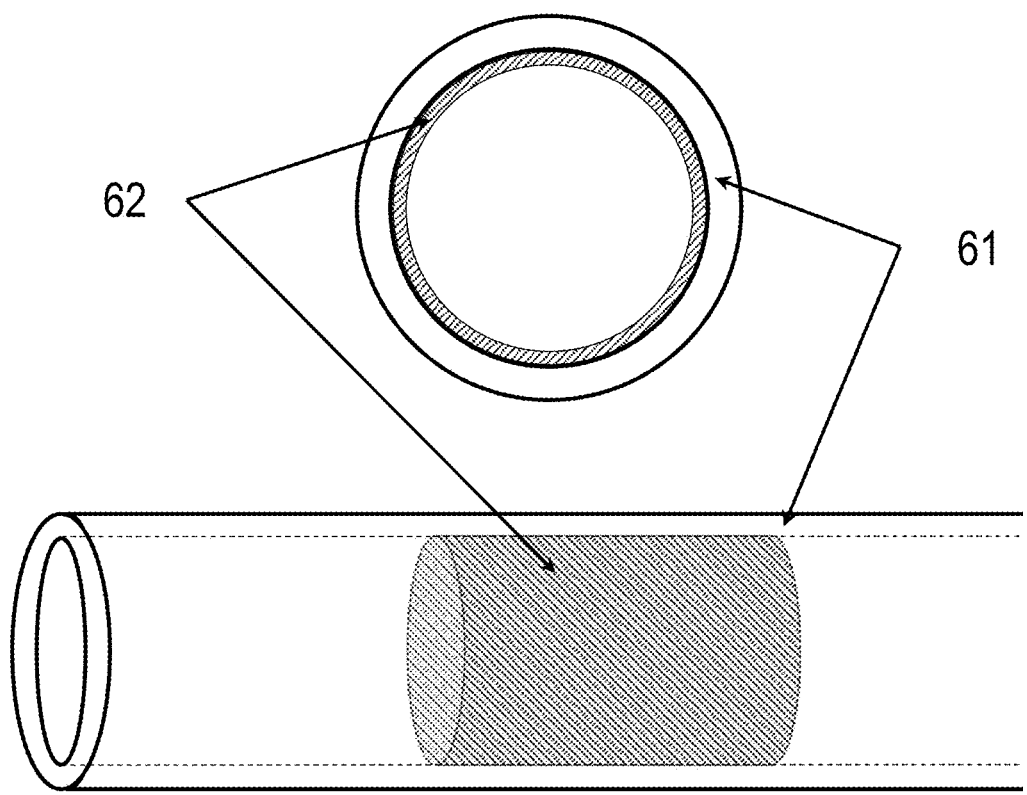
FIG. 6 shows end view and side view of an evanescent field sensing element according to one or more embodiments.

In one or more embodiments, the evanescent field sensing element may have a shape of a curved surface, covering at least a certain length of a downhole structure. FIG. 6 shows an arrangement of an evanescent field sensing element according to one or more embodiments. An evanescent field sensing element 62 having a tubular (or hollow cylinder) shape may be arranged inside a downhole structure 61. The evanescent field sensing element may be attached to an inner wall of the downhole structure, or in some embodiments, the evanescent field sensing element may also be used as a portion of the downhole structure. The evanescent field sensing element covers at least a certain length and a certain depth of the downhole structure along a flow direction of downhole fluids.

According to one or more embodiments, the system for monitoring a downhole composition may include a plurality of evanescent field sensing elements arranged in series and attached to an inner surface of a downhole structure. Such configuration effectively enhances fluid mixing by increasing turbulence and reduces the influence of the boundary layer on the sensing. When the inner surface of the downhole structure is smooth, a laminar flow of downhole compositions forms with a lower velocity near the inner surface. As such, if a single sensing element is disposed near the inner surface, the monitoring results may not accurately reflect the downhole compositions. Arranging the plurality of evanescent field sensing elements in series effectively introduces turbulence and increases mixing of downhole compositions. Along a flow direction of downhole compositions, each precedent evanescent field sensing element may contribute to a turbulent flow and facilitates detection of the following evanescent field sensing elements. Any of the previously described shapes of sensing elements, as described in FIGS. 1-6, may be arranged in series along a downhole structure to enhance fluid mixing. Any number of the previously described sensing elements may be used in any combination to achieve sufficient fluid mixing.

In one or more embodiments, the evanescent field sensing element may be a few-mode or multimode optical fiber, or a crystal with total or partial internal reflection made of silica ($SiO_2$), fluorine-doped $SiO_2$ ($F:SiO_2$), sapphire, silicon carbide (SiC), alumina, titanium nitride (TiN), or other materials providing partial or total internal reflection. The crystal used as evanescent field sensing element may be germanium (Ge), zinc selenide (ZnSe), zinc sulfide (ZnS), thallium bromides (e.g., KRS-5), or (Si). The excellent mechanical properties of diamond make it an ideal material as evanescent field sensing element, with the broad diamond phonon band between 2600 and 1900 $cm^{-1}$ significantly decreasing signal-to-noise ratio in this region. Other waveguides may be used, including but not limited to glass fibers (e.g., chalcogenides, fluorides), (poly)crystalline fibers (e.g., silver halides, sapphire), hollow waveguides (e.g., hollow silica or sapphire tubes) filled with a gas (e.g., air, nitrogen, or helium), and solid waveguides (e.g., thin film planar GaAs/AlGaAs).

In one or more embodiments, a modification layer may be coated, added, or patterned to modify the surface of the evanescent field sensing element. The modification layer may be a protective layer, a sensitivity enhancing layer, a self-cleaning layer, or a combination thereof. The modification layer may be made of polymers, ceramics, oxides, diamond, metals, meta-materials, or other materials as required by their functions. In one or more embodiments, the modification layer may be composed of fluoropolymers (e.g. PVDF, PTFE), diamond, diamond like carbon-based materials, oxides (e.g., $ZrO_2$, $HfO_2$, $TiO_2$, quartz), nitrides (e.g., TiN, AN), carbides (e.g., SiC), or a combination thereof. The sensitivity enhancing layer may modify the propagation of evanescent waves and enhance sensing capabilities by providing continuous evanescent wave along the surface and avoid generation of discrete evanescent waves. The thickness of the modification layer may be adjusted accordingly as needed. A self-cleaning layer may be coated to improve stability and durability of evanescent field sensing element or the waveguide. Under extreme conditions, for example measurements in a wellbore of oil production, a robust sensing system is required for sampling and analysis. A self-cleaning material treated surface is configured to be omniphobic or super omniphobic so that repels water and oil or switchable between hydrophobic and oleophobic, minimizing the damage from hazardous and extreme environments.

Figure 7:
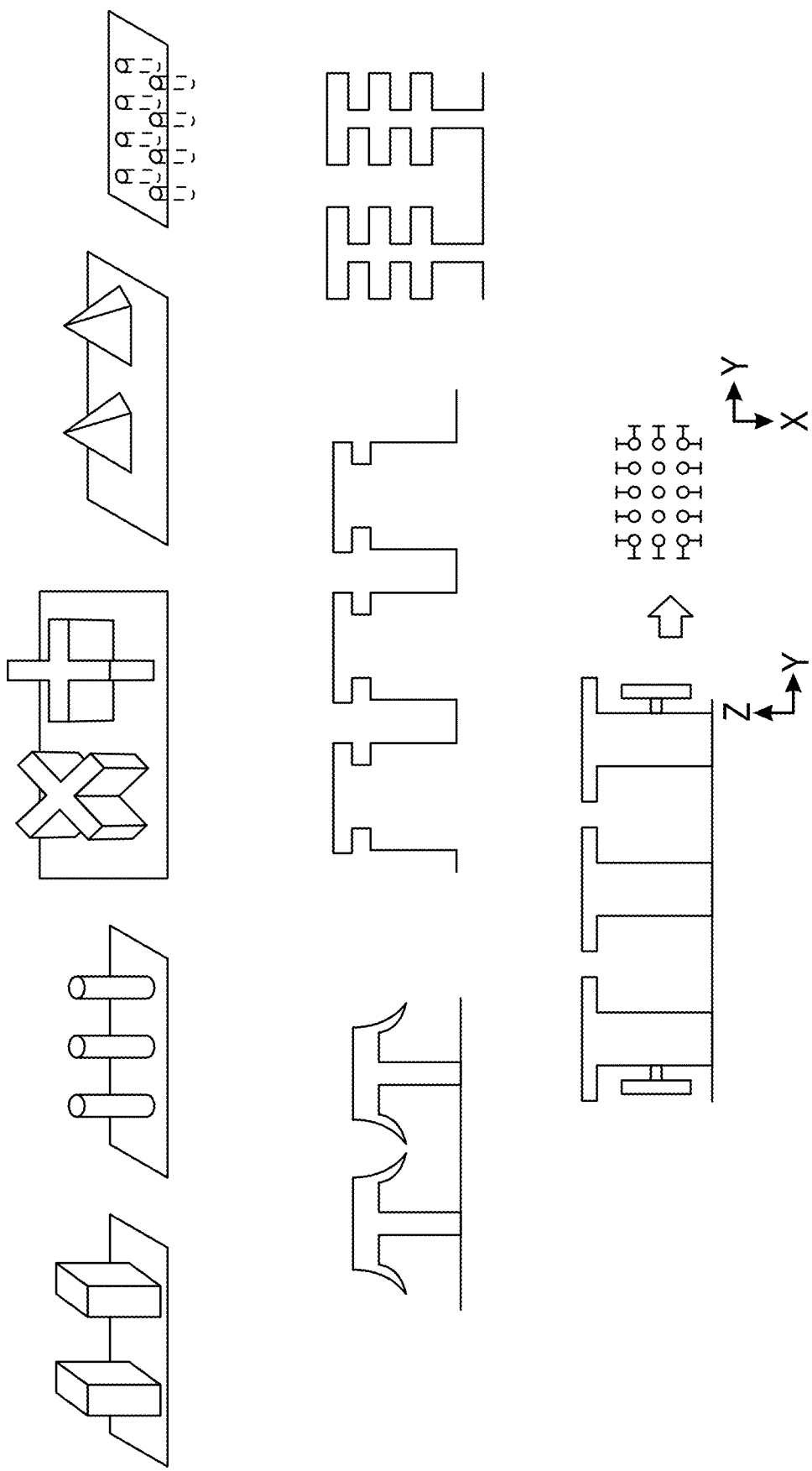
FIG. 7 shows microstructures according to one or more embodiments.

In one or more embodiments, the modification layer may be meta-materials or meta-surfaces in forms of a 1-dimensional or 2-dimensional array of microstructures of particular shape, such as cube, cylinder, cross, cone, cavity, prism, T-shape, etc. Examples of the array of microstructures are shown in FIG. 7, but the configuration of the microstructures are not limited to these examples. The meta-materials or meta-surfaces may be formed by directly patterning on the evanescent field sensing element through laser patterning, plasma etching, chemical etching, or other methods. When the periodicity and/or dimensions of the microstructures are in a dimension similar to the wavelength of the evanescent field, the electromagnetic properties may be enhanced, resulting in enhanced sensitivity. When the microstructures have a dimension of about 1 to 500 µm, they may serve as a self-cleaning layer. In one or more embodiments, the modification layer formed by meta-materials or meta-surfaces may serve one or more functions.

According to one or more embodiments, the system for monitoring a downhole composition may comprise a waveguide to direct an incident beam from an electromagnetic source to the evanescent field sensing element and direct a fingerprint beam from the evanescent field sensing element to a detector. In one or more embodiments, the waveguide may also be used to connect a plurality of evanescent field sensing elements. In one or more embodiments, the waveguide may be used as the evanescent field sensing element at positions of interest. In one or more embodiments, the waveguide portion serving as the evanescent field sending element may be functionalized with the modification layer.

According to one or more embodiments, the system for monitoring a downhole composition may comprise an electromagnetic source capable of emitting an incident beam at a single or multiple wavelengths (that is, single-band or wide-band). The electromagnetic source may be selected from lamps, lasers, light-emitting diodes (LEDs), superluminescent diodes (SLEDs), blackbody radiators, antennas, or plasma sources. The electromagnetic source may be continuous or pulsed.

According to one or more embodiments, the system for monitoring a downhole composition may comprise a frequency comb generator (e.g., a resonator having resonant cavities) to generate a beam with optical frequency comb (OFC), when a coherent laser is used as electromagnetic source. A coherent beam with OFC provides higher brightness, increased signal-to-noise ratio, and decreased measurement time. In one or more embodiments, an OFC beam is directed to the evanescent field sensing element and serves as the incident beam. The spectrum of the OFC beam includes a series of discrete, equally spaced frequency lines, and the intensity of comb lines may vary substantially. The OFC beam may be generated by periodic modulation (in amplitude and/or phase) of a continuous-wave laser, four-wave mixing in nonlinear media, or stabilizing a train of pulses generated by a mode-locked laser. For example, a non-linear optical resonator having resonant cavities can be used in conjunction with pulsed laser sources to generate the OFC beam. The non-linear optical resonator can non-linearly transform a beam from a continuous laser with a single frequency to the OFC beam with multiple frequencies.

The use of OFC may provide: improved selectivity and sensitivity with ensured thermal and mechanical stability; well-resolved absorption and dispersion spectra recorded simultaneously; and sensitive detection of multiple chemical species over a broad spectral window. OFC may be utilized at a wide range of frequencies extending from the terahertz to the UV region. Its high spatial coherence allows for longer interrogation paths, higher sensitivity, high frequency resolution, and high accuracy. The aforementioned features of OFC may allow dynamic and real-time sensing with high speed of spectrum and data acquisition and instant feedback to control devices for optimization of oil production.

According to one or more embodiments, the system for monitoring a downhole composition may comprise an electromagnetic wavelength selector, such as a dispersive, dichroic, or bandpass optical or electro-optical element, to select single or multiple frequencies of interest.

According to one or more embodiments, the system for monitoring a downhole composition may comprise a coupler, an optical switch, or a beam splitter to split a beam generated from the electromagnetic source into two or more beams, or to combine two or more beams into one beam. In one or more embodiments, a portion of the beam may serve as an incident beam and is directed to the evanescent field sensing element, where a fingerprint beam is formed after interaction with downhole composition. The rest of the beam, which is not directed to the evanescent field sensing element, may serve as a reference beam. In one or more embodiments, the difference of the reference beam and the fingerprint beam may reflect the chemical fingerprints of downhole compositions. In one or more embodiments, the reference beam and the fingerprint beam are combined to form an interferring beam reflecting the chemical fingerprints of downhole compositions. In one or more embodiments, both the sensing beam and the reference beam may couple to a resonator to generate frequency comb. In one or more embodiments, the system for monitoring a downhole composition may comprise an amplifier.

In one or more embodiments, the system for monitoring a downhole composition may use two OFC beams with slightly different comb tooth spacing, namely dual-comb spectroscopy (DCS). A beam generated from an electromagnetic source may be split into a reference beam and an incident beam, both modified by a resonator (e.g., Kerr frequency comb microresonator) to generate OFC. The incident OFC beam is directed to the evanescent field sensing element for interaction with downhole compositions. The interaction modifies the intensity and spectral distribution of the incident OFC beam, causing a slightly different repetition frequency thus generating a fingerprint OFC beam. The reference OFC beam and the fingerprint OFC beam are subsequently recombined using a recombiner, generating a recombined beam with an interferogram spectrum that interferes with both the reference OFC beam and the fingerprint OFC beam. In one or more embodiments, the recombined beam is recorded as a function of time and may be Fourier transformed to reveal the spectrum. The line spacing of the interferogram spectrum is converted to a radio frequency (RF) signal whose signatures reflect the chemical fingerprints of downhole compositions. The information containing the fingerprints is then feedback to a controller for control and optimization of downhole compositions.

In one or more embodiments, the system for monitoring a downhole composition may comprise a detector. In one or more embodiments, the detector may be a dispersive spectrometer allowing detection at different wavelengths. The dispersive spectrometer may couple with virtual imaging phase array (VIPA) to achieve a time resolution at microseconds, allowing dynamic and real-time monitoring of chemical fingerprints. In one or more embodiments, a single detector without dispersive elements may be utilized. In one or more embodiments, the detector may be a cooled (solid state) or uncooled photodiode or a photoelectric sensor. The type of the detector depends primarily on the range of wavelengths to be measured. For example, silicon-based charge-coupled devices (CCDs) are suitable for UV, visible, and the shorter end of the IR range. For detection at longer wavelengths, an IR detector may be used. The IR detector may be photodetectors (photon detectors) which are sensitive in a relatively long wavelength region, or thermal detectors based on sensing small temperature changes induced by absorption of IR light. In one or more embodiments, semiconductor materials with a lower band gap energy may be used in the detector, such that photons with lower energy are sufficient to create a carrier which contribute to photocurrent. Indium gallium arsenide (InGaAs) detectors are suitable for wavelengths up to ≈1.7 µm. Germanium (Ge) photodiodes can be used at about 0.9 µm to 1.6 µm. For wavelengths beyond 5 µm, indium antimonide (InSb) photodiodes may be used. The IR detector may be a mercury cadmium telluride (MCT) detector, quantum dot infrared photodetectors (QDIPs), or quantum well infrared photodetectors (QWIPs) based on GaAs/AlGaAs. A thermal IR detector may include pyroelectric detectors based on ferroelectric materials such as lithium tantalate, or bolometers containing a thin IR-absorbing plate made of amorphous silicon or vanadium oxide. Alternatively, detectors with up converting crystals, such as lithium niobite, or nanoparticles could be used as sensors with lower temperature noise sensitivity. In one or more embodiments, the detector may be a scintillation detector (e.g., sodium iodide detector).

In one or more embodiments, the system for monitoring a downhole composition may comprise a detector based on Fourier transform spectroscopy (FTS). FTS uses mathematical process (Fourier transform) to translate a raw data into an actual spectrum including information of chemical fingerprints. In one or more embodiments, FTS may use an interferometer to generate a wide band interferogram in the time-domain whose Fourier transform is the optical spectrum. Laser arrays or wide band electromagnetic sources, capable of switching rapidly through fibers of different lengths, may provide the time delay required to capture the time-domain interferogram for FTS. In one or more embodiments, the detector based on FTS may include optical spectroscopy, infrared spectroscopy (FTIR), nuclear magnetic resonance (NMR), magnetic resonance spectroscopic imaging (MRSI), mass spectrometry and electron spin resonance spectroscopy. In one or more embodiments, the FTS may be associated with a microprocessor, performing calculation using algorithms to identify or correlate spectral information (i.e., peak positions and intensities) to the downhole compositions, as well as desired properties of downhole fluids such as density and viscosity. Instead of transmitting the full spectral information, data transmitted may be compressed into only the relevant information.

In one or more embodiments, the system for monitoring a downhole composition may comprise a detector based on FTS including a Michelson interferometer. The Michelson interferometer measures, on a single photo detector, an interference between two time-delayed signals from two arms as a function of the optical path difference. The time-domain interferogram may be obtained with mirrors on movable arms. In one or more embodiments, the fingerprint beam may be directed into the Michelson interferometer containing a certain configuration of mirrors, at least one of which is movable using a motor.

In one or more embodiments, the system for monitoring a downhole composition may comprise an electromagnetic source, a waveguide (e.g., optical fiber), an evanescent field sensing element, and a detector. In one or more embodiments, the electromagnetic source and the detector may be disposed above ground in a derrick. The waveguide directs an incident beam to the one or more subterranean evanescent field sensing element and directs a fingerprint beam to the detector.

In one or more embodiments, a beam generated from the electromagnetic source may be split into a plurality of beams for monitoring at different positions or depths. In one or more embodiments, each of the beams may serve an incident beam for interaction at an interface between the evanescent field sensing element and downhole compositions to form a fingerprint beam. Each fingerprint beam is directed to a detector for analysis of fingerprint information. Alternatively, a plurality of fingerprint beams may be combined and directed to the detector. In one or more embodiments, a part of the plurality of beams may serve as incident beams and the others may serve as reference beams. The incident beams are directed to the evanescent field sensing elements for interaction with downhole compositions, forming fingerprint beams. The fingerprint beams and reference beams may be detected, and a difference reflects the chemical fingerprint of downhole compositions. Alternatively, the reference beam may be recombined with the fingerprint beam, generating a recombined beam having an interferogram spectrum (an interfering beam), and directed to the detector.

Figure 8:
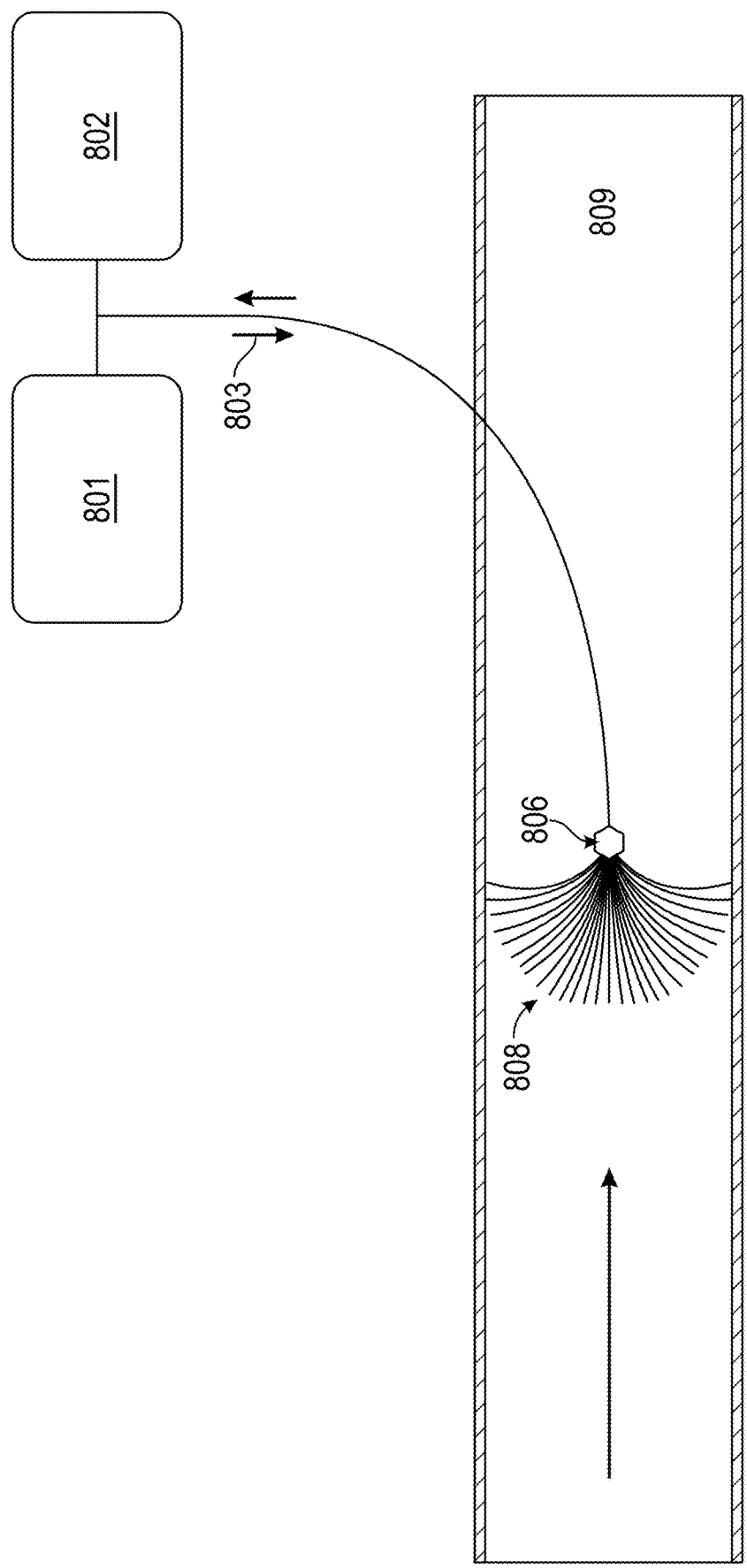
FIG. 8 shows a system of monitoring a downhole composition in a wellbore according to one or more embodiments.

FIG. 8 shows a system for monitoring a downhole composition according to one or more embodiments. An electromagnetic source 801 may be used to generate a beam, with at least a part of the beam is directed downhole to a tubular structure 809 through a waveguide 803. The waveguide may comprise a single optical fiber or an optical fiber bundle array. When a single optical fiber is used, a 1×n coupler 806 may be used to split the beam into a plurality of incident beams. When an optical fiber bundle array is used, no coupler is needed. The incident beams are directed along n optical fibers 808, each comprising one or more evanescent field sensing elements exposed to downhole compositions. After reaction with downhole compositions, fingerprint beams containing information of chemical fingerprints are collected by the n optical fibers, recombined, and directed to a detector 802 through the waveguide 803. The n optical fibers may be distributed in any shape or configuration, arranging the evanescent field sensing elements at different positions and different depth. In one or more embodiments, the optical fibers may be distributed to fan-like configuration to probe simultaneously downhole compositions at different radial positions, or in series along the flow direction.

Figure 9:
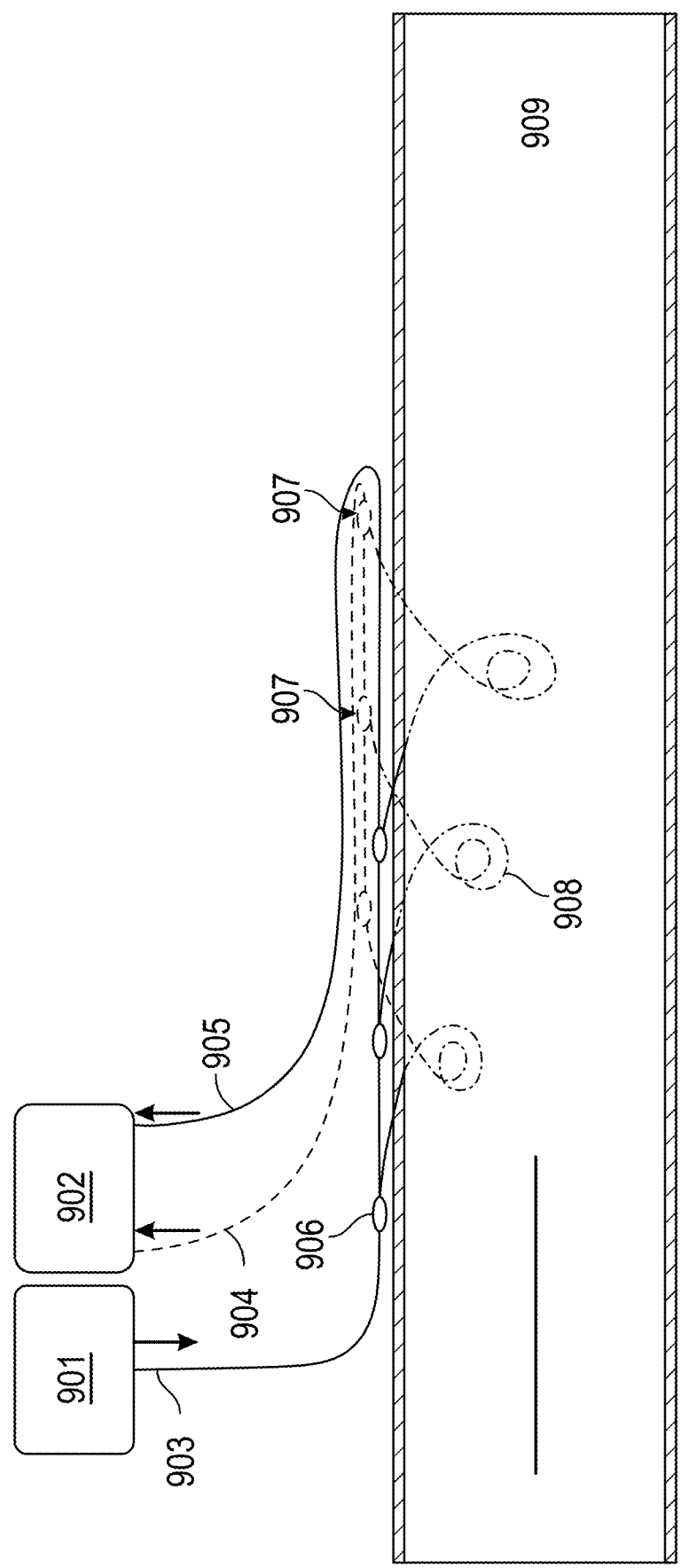
FIG. 9 shows a system of monitoring a downhole composition in a wellbore according to one or more embodiments.

FIG. 9 shows a system for monitoring a downhole composition according to one or more embodiments. An electromagnetic source 901 may be used to generate a beam directed downhole to a tubular structure 909 through a waveguide (e.g., optical fiber) 903. The beam may be split by a 1×2 coupler 906 into a reference beam and an incident beam. The incident beam is directed to one or more evanescent field sensing elements exposed to downhole compositions through optical fibers 908. In one or more embodiments, the system comprises a plurality of 1×2 couplers to distribute a plurality of incident beams to different positions. After interaction with the downhole compositions, the plurality of fingerprint beams containing information of chemical fingerprints are recombined by 2×1 couplers 907 and directed to a detector 902 through an input waveguide 904. The reference beam that is not directed to any of the evanescent field sensing elements is also directed to the detector through a return waveguide 905. The evanescent field sensing elements may have any aforementioned shape or configuration according to one or more embodiments of the present disclosure, and may be arranged at different positions and different depths. In one or more embodiments, both the reference beam and the incident beam are modified to an OFC beam.

In one or more embodiments, the system for monitoring a downhole composition may comprise a control unit for control and optimization of downhole production. The control unit may be controlled by production personnel, production algorithms, or other systems of interest. In one or more embodiments, the control unit may be an inflow and injection control device (ICD) that controls actuation to optimize the downhole production. The ICD may be an electrical actuator, a fluid actuator, a mechanical actuator, or the like.

In one or more embodiments, a beam, for example a fingerprint beam or a reference beam, may be converted to an electrical signal for analysis via an opto-electrical detector or an array thereof (e.g., thermopile, photodetector, pyroelectric detector, electrocaloric detector, microbolometer, diode, pyrometer, or radiometer). A digitizer may be used in addition, in order to digitalize the signals obtained from a detector.

Figure 10:
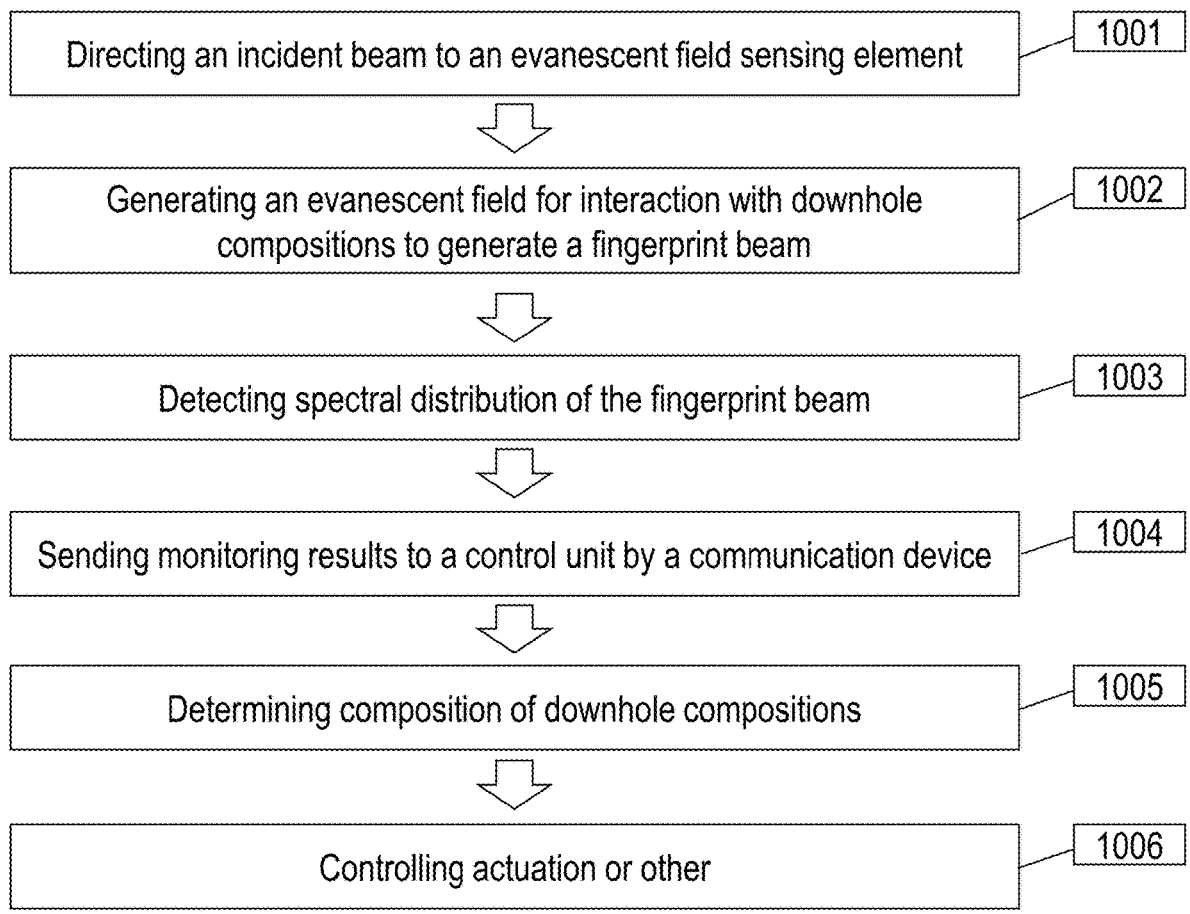
FIG. 10 shows a method of monitoring a composition in a wellbore according to one or more embodiments.

In one or more embodiments, the system for monitoring a downhole composition may comprise a communication device that receives the real-time chemical fingerprints monitoring results from the detector and provide feedback information to the control unit for instant operation decisions based on compositions of produced oil in the wellbore. A method of monitoring a downhole composition according to one or more embodiments is provided in FIG. 10. Prior to step 1001, the previously described evanescent field sensing elements are placed downhole at a desired position at certain depth. Then, a beam is generated from an electromagnetic source. In one or more embodiments, the beam may optionally pass through one or more of a beam splitter, a coupler, an optical switch, a frequency comb generator, a circulator, and an amplifier. At least a portion of the beam is guided to an evanescent field sensing element using a waveguide, serving as an incident beam for reaction with downhole compositions. A plurality of beams may be employed, either as incident beams or reference beams. At step 1002, the incident beam interacts with downhole compositions at the interface of the evanescent field sensing elements and downhole compositions. An evanescent field is generated at the interface, enabling interaction to form a fingerprint beam containing information of chemical fingerprints of downhole compositions. Step 1003 includes a step of detecting spectral distribution of the fingerprint beam. The fingerprint beam is directed to a detector, either in-situ or above ground, to capture the chemical fingerprints in real-time. At step 1003, the spectrum collected by the detector is analyzed to determine the compositions, including type of oils, water cut, gases, and other chemicals used in the production process. At step 1004, a communication device sends the monitoring results to a control unit and the control unit controls actuation to optimize the downhole production. At step 1005, the composition or compositional changes of the downhole production may be monitored in real-time and in-situ. A determination of whether the expected composition is achieved is made at step 1006 based on the monitoring results. If the expectation is met with regard to the composition of downhole production, a report may be created of the chemical composition of the actuated segments. Otherwise, monitoring may continue by circle back to step 1002.

While the system according to one or more embodiments described above are associated with downhole structures and applications, a person having ordinary skill in the art would appreciate that the system would also apply to surface applications for flowline monitoring, or other applications where monitoring a composition is desired.

EXAMPLES

The following examples are merely illustrative and should not be interpreted as limiting the scope of the present disclosure.

Example 1

Figure 11A:
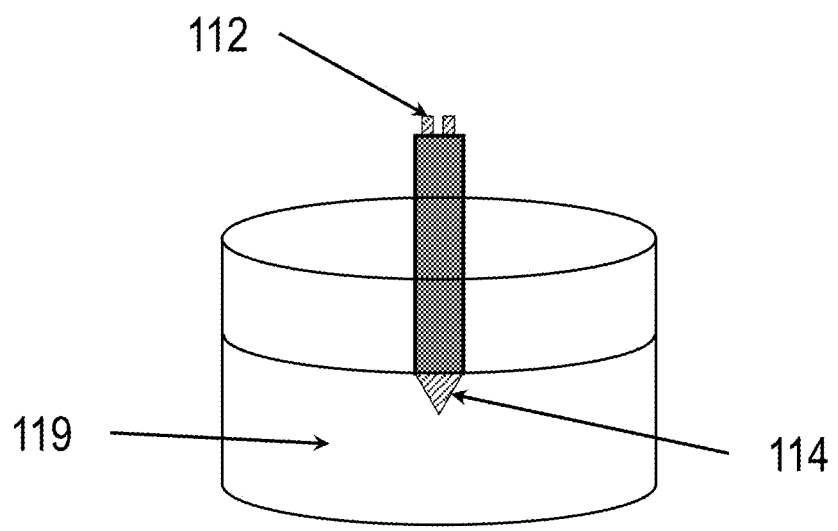
FIGS. 11A and 11B show a system comprising an evanescent field sensing element and monitoring results obtained from the evanescent field sensing element according to one or more embodiments.

As a first example, the system of monitoring a downhole composition may comprise an evanescent field sensing element having a point configuration. The system shown in FIG. 11A comprises a waveguide 112 formed by silver halide and chalcogenide glass directing near infrared to far infrared radiation to an evanescent field sensing element 114 formed by a diamond/zirconia tip, for monitoring carbon dioxide concentration in a solution 119. The detector used herein is a cooled MCT detector. The evanescent field sensing element having a point configuration and a diameter of millimeters was inserted into a serious of solutions (#1 to #7) comprising mixtures of water ($H_2O$) and carbon dioxide ($CO_2$). Solution #1 was a saturated solution of $CO_2$ obtained by bubbling $CO_2$ into $H_2O$ at 30° C. and 1002 hPa (hectopascal) for certain period of time (e.g., minutes). Solution #1 had a $CO_2$ concentration of 450 ppm. Solution #2 was obtained by diluting solution #1 such that the $CO_2$ concentration in solution #2 was a half of the $CO_2$ concentration in solution #1. Solutions #3 to #7 were obtained by series dilution in a similar manner. The $CO_2$ concentration in solutions #1-#7 were 450, 225, 113, 56, 28, 14, and 7 ppm, respectively.

Figure 11B:
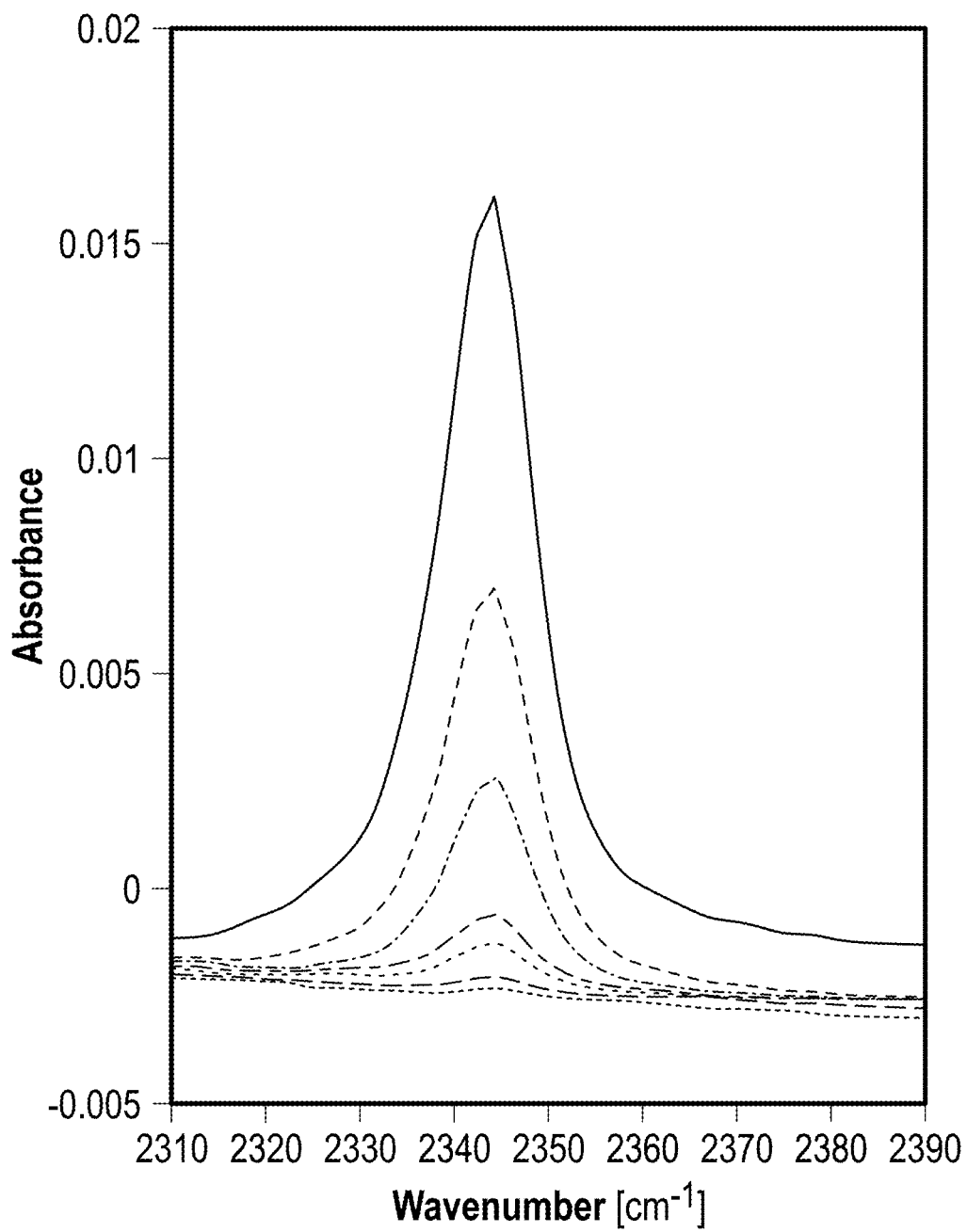

The IR spectra of the series solutions are shown in FIG. 11B. All spectra showed a strong absorption band caused by asymmetrical C=O stretching around 2342 $cm^{-1}$ corresponding to a wavelength of 4.3 μm. The peaks at 2342 $cm^{-1}$ were used to quantify the amount of $CO_2$ in the solutions. The detection limit reached as low as 7 ppm.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims, except for those in which the claim expressly uses the words 'means for' together with an associated function.

What is claimed:

1. A system for monitoring a composition, the system comprising:
   an electromagnetic source that emits a beam;
   one or more evanescent field sensing element inside a tubular structure, arranged in series along a flow direction of the composition generating turbulence, and configured to be in direct contact with the composition;
   a waveguide that directs at least a portion of the beam to the evanescent field sensing element as an incident beam;
   wherein
      the evanescent field sensing element provides partial or total internal reflection of the incident beam at an interface between the evanescent field sensing element and the composition, and
      the incident beam interacts with the composition to form a fingerprint beam;
   a coupler that splits the beam, such that at least a portion of the beam serves as a reference beam without passing through the evanescent field sensing element;
   at least one frequency comb generator that modifies both the reference beam and the incident beam with optical frequency comb (OFC); and
   a detector configured to obtain a spectral distribution of the fingerprint beam.

2. The system according to claim 1, wherein the evanescent field sensing element has a shape selected from the group consisting of point, line, prism, cylinder, tube, ring, helix, and combinations thereof.

3. The system according to claim 1, further comprising a second coupler that recombines the fingerprint beam and the reference beam to form the interacted beam having an interferogram.

4. The system according to claim 1, wherein the detector is a Fourier transform spectrometer or at least one photodiode.

5. The system according to claim 1, wherein the electromagnetic source is an array of lasers or a wide-band light source that emit the beam having a range of frequency.

6. The system according to claim 1, wherein the evanescent field sensing element is at least one of the following: a crystal with or partial or total internal reflection, an optical fiber, a waveguide, a meta-surface, and a meta-material.

7. The system according to claim 1, wherein a surface of the evanescent field sensing element further comprises a modification layer of at least one of the following: a protective layer, a sensitivity enhancing layer, and a self-cleaning layer.

8. The system according to claim 1, wherein the evanescent field sensing element is modified with meta-materials or meta-surfaces in forms of a 1-dimensional or 2-dimensional array of microstructures of particular shape.

9. A method for monitoring a composition, the method comprising:
   placing one or more evanescent field sensing element in series along a flow direction of the composition;
   contacting the evanescent field sensing element with the composition such that, due to the arrangement of the evanescent field sensing element in series along the flow direction, turbulence in the composition is generated;
   generating a beam from an electromagnetic source;
   splitting the beam into a reference beam and an incident beam;
   modifying the reference beam and the incident beam with at least one frequency comb generator;

directing the incident beam to the evanescent field sensing element;

generating an evanescent field at an interface between the evanescent field sensing element and the composition, where the incident beam interacts with the composition to form a fingerprint beam;

recombining the reference beam and the fingerprint beam; and detecting spectral distribution of the fingerprint beam using a Fourier transform spectrometer or at least one photodiode to monitor the composition in real-time; and transmitting the spectral distribution to a control unit.

10. The method according to claim 9, further comprising:
prior to placing the evanescent field sensing element, modifying the evanescent field sensing element with at least one of the following: a protective layer, a sensitivity enhancing layer, and a self-cleaning layer.

11. The method according to claim 9, wherein the evanescent field sensing element have a shape selected from the group consisting of point, line, prism, cylinder, tube, ring, helix, and combinations thereof.

12. The method according to claim 9, wherein the evanescent field sensing element is modified with meta-materials or meta-surfaces in forms of a 1-dimensional or 2-dimensional array of microstructures of particular shape.

* * * * *